US00PP22818P2

(12) United States Plant Patent
Smith

(10) Patent No.: US PP22,818 P2
(45) Date of Patent: Jun. 26, 2012

(54) ***CHRYSANTHEMUM* PLANT NAMED 'SYEMA CORBI'**

(50) Latin Name: *Chrysanthemum×morifolium*
Varietal Denomination: Syema Corbi

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/065,176

(22) Filed: Mar. 16, 2011

(51) Int. Cl.
*A01H 5/00* (2006.01)

(52) U.S. Cl. ..... Plt./287

(58) Field of Classification Search ..... Plt./287, Plt./293
See application file for complete search history.

*Primary Examiner* — Annette Para
(74) *Attorney, Agent, or Firm* — Joshua L. Price

(57) ABSTRACT

A new *Chrysanthemum* plant named 'Syema Corbi' particularly distinguished by the large, two-toned red colored inflorescences, dark yellow-green foliage, nicely mounded plant habit with a late natural flowering season of about mid October.

1 Drawing Sheet

Latin name of the genus and species of the plant claimed: *Chrysanthemum×morifolium.*

Varietal denomination: 'Syema Corbi'.

BACKGROUND OF THE NEW PLANT

The present invention comprises a new *Chrysanthemum*, botanically known as *Chrysanthemum×morifolium*, and hereinafter referred to by the variety name 'Syema Corbi'.

'Syema Corbi' is a product of a planned breeding program. The new cultivar has large, two-toned red colored inflorescences, dark yellow-green foliage, nicely mounded plant habit with a late natural flowering season of about mid October.

'Syema Corbi' originates as a natural whole plant mutation of 'Empire Emma', U.S. Plant Pat. No. 20,196, and was discovered and selected by the inventor as a single flowering plant within a population of the parent cultivar in a controlled breeding program in Alva, Fla. in November 2007. The parent cultivar 'Empire Emma' has a little larger inflorescence size, little larger plant size, more bronze inflorescence color, and a natural season flowering that is a couple days faster.

The first act of asexual reproduction of 'Syema Corbi' was accomplished when vegetative cuttings were propagated from the initial selection in December 2007 in a controlled environment in Alva, Fla.

BRIEF SUMMARY OF INVENTION

Horticultural examination of plants grown from cuttings of the plant initiated in December 2007 and continuing thereafter, has demonstrated that the combination of characteristics as herein disclosed for 'Syema Corbi' are firmly fixed and are retained through successive generations of asexual reproduction.

'Syema Corbi' has not been observed under all possible environmental conditions. The phenotype may vary significantly with variations in environment such as temperature, light intensity and day length.

A Plant Breeder's Right for this cultivar has been applied for in Canada on Mar. 19, 2010 (No. 10-6893). 'Syema Corbi' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Syema Corbi' with colors being as true as possible with an illustration of this type. The photographic drawing shows a flowering potted plant of the new variety.

DETAILED BOTANICAL DESCRIPTION

The plant used for the photographs was about 16 weeks old grown in Monroeville, N.J. in an outdoor trial. One rooted cuttings grown in a nine inch pot with no terminal pinching of the apices. The photograph was taken in mid October 2010 in New Jersey.

The plant descriptions and measurements were taken in Gilroy, Calif. in May 2010 under natural light. Plants were grown under conditions which approximate those generally used for potted *chrysanthemum* trials in a greenhouse. These plants used in the descriptions were about 10 weeks old grown in 4.5 inch pots.

Color references are made to The Royal Horticultural Society Colour Chart (R.H.S.) 2001.

TABLE 1

DIFFERENCES BETWEEN THE NEW VARIETY 'SYEMA CORBI' AND A SIMILAR VARIETY

| | 'Syema Corbi' | 'Estrada' (U.S. Plant Pat. No. 15,436) |
|---|---|---|
| Inflorescence color: | Two-toned | Single color |
| Inflorescence size: | Larger | Smaller |
| Plant size: | Little smaller | Little larger |
| Natural season response: | Few days slower | Few days faster |

TABLE 1-continued

DIFFERENCES BETWEEN THE NEW VARIETY 'SYEMA CORBI' AND A SIMILAR VARIETY

| | 'Syema Corbi' | 'Estrada' (U.S. Plant Pat. No. 15,436) |
|---|---|---|
| Shaded flowering response: | About 10 days slower | About 10 days faster |

Plant:

*Form, growth and habit*.—Herbaceous decorative garden-type, stems upright, freely branching, strong and moderately vigorous growth habit.

*Plant height*.—11-13 cm.

*Plant height* (*inflorescence included*).—18-21 cm.

*Plant width*.—17-18 cm.

*Garden performance and tolerance to weather*.—Very good.

*Crop time to flowering*.—About 10 weeks.

Roots:

*Number of days to initiate roots*.—4 days at about 22 degrees C.

*Number of days to produce a rooted cutting*.—10-12 days at 22 degrees C.

*Type*.—Fine, fibrous, free branching.

*Color*.—RHS N155B but whiter.

Foliage:

*Arrangement*.—Alternate.

*Immature, leaf color, upper surface*.—RHS 147A but darker.

*Lower surface*.—Closest to RHS 137A.

*Mature, leaf color, upper surface*.—RHS 147A but darker.

*Lower surface*.—Closest to RHS 137A.

*Length*.—4.3-4.5 cm.

*Width*.—3.4-4.0 cm.

*Shape*.—Ovate.

*Base shape*.—Attenuate.

*Apex shape*.—Mucronulate.

*Margin*.—Irregularly lobed; very slightly palmate; slightly serrate.

*Texture, upper surface*.—Bifid T-shaped hairs.

*Lower surface*.—Bifid T-shaped hairs.

*Color of veins, upper surface*.—RHS 138B.

*Color of veins, lower surface*.—RHS 138B.

*Petiole color*.—RHS 138B.

*Length*.—0.6-0.8 cm.

*Diameter*.—0.3 cm.

*Texture*.—Bifid T-shaped hairs.

Stem:

*Quantity of main branches per plant*.—4-5.

*Color of stem*.—RHS 137A but appears lighter because of hairs.

*Length of stem*.—8-10 cm.

*Diameter*.—0.3-0.35 cm.

*Length of internodes*.—0.5-1.0 cm.

*Texture*.—Bifid T-shaped hairs.

*Color of peduncle*.—RHS 137A but appears lighter because of hairs.

*Length of peduncle*.—4.0-7.0 cm.

*Peduncle diameter*.—0.15-0.2 cm.

*Texture*.—Bifid T-shaped hairs.

Inflorescence:

*Type*.—Compositae type, solitary decorative-type inflorescence, borne terminally above foliage, ray florets arranged acropetally on a capitulum.

*Quantity of short days to flowering* (*response time*).—About 59 days.

*Quantity of inflorescences per plant*.—Approximately 40 and numerous buds,

*Lastingness of individual blooms on the plant*.—About 5 weeks from first inflorescence.

*Fragrance*.—Slightly spicy.

Bud (just when opening/showing color):

*Color*.—Closest to RHS 181C.

*Length*.—0.8-1.0 cm.

*Width*.—1.2 cm.

*Shape*.—Oblate.

Immature inflorescence:

*Diameter*.—Approximately 4.0-5.0 cm.

*Color of ray florets, upper surface*.—Between RHS 181A and RHS 181B.

*Lower surface*.—RHS 181B with margins RHS 181A.

Mature inflorescence:

*Diameter*.—6.5 cm.

*Depth*.—2.0 cm.

*Total diameter of 'disc'*.—0.3 cm.

*Receptacle height*.—0.3 cm.

Receptacle diameter.—0.5-0.6 cm.

Ray florets:

*Average quantity of florets*.—Approximately 200-250 in numerous whorls.

*Color of florets, upper surface*.—Closest to RHS N170D base; overlaid RHS 51C to RHS 51B towards the margins, and close to RHS 181C to RHS 181B basally in almost a cross-hatched pattern and longitudinal at the margins.

*Lower surface*.—RHS N170D base; overlaid RHS 51C in almost a cross-hatched pattern and longitudinal at the margins.

*Length*.—2.8-3.5 cm.

*Width*.—0.5-0.8 cm.

*Shape*.—Elliptical.

*Apex shape*.—Irregularly emarginate.

*Margin*.—Entire.

*Texture, upper surface*.—Papillose.

*Lower surface*.—Papillose.

Disc florets:

*Average quantity of florets*.—About 20.

*Color of florets*.—RHS 1C but lighter; RHS 1A apex.

*Length*.—0.4 cm.

*Width*.—0.1 cm.

*Shape*.—Tubular, elongated.

*Apex shape*.—Acute, 5 pointed.

Phyllaries:

*Quantity*.—About 30.

*Color, upper surface*.—RHS 137A.

*Lower surface*.—RHS 137A but appears lighter because of hairs.

*Length*.—0.5-0.7 cm.

*Width*.—0.2 cm.

*Shape*.—Lanceolate.

*Apex shape*.—Acute.

*Based*.—Fused.

*Margins*.—Entire; papery.

*Texture, upper surface*.—Smooth.

*Lower surface*.—Bifid T-shaped hairs.

Reproductive organs:

*Pistil.*—1.

*Length.*—0.5 cm.

*Style color.*—RHS 1C.

*Style length.*—0.4 cm.

*Stigma color.*—RHS 7A.

*Stigma shape.*—Bi-parted.

*Ovary color.*—Not observed.

*Stamens.*—1.

*Color of filaments.*—RHS 2B.

*Length filaments.*—0.3 cm.

*Anther color.*—RHS 14A.

*Anther length.*—0.1 cm.

*Anther shape.*—Oval.

*Color of pollen.*—Not observed.

*Pollen amount.*—Not observed.

*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Syema Corbi' substantially as illustrated and described herein.

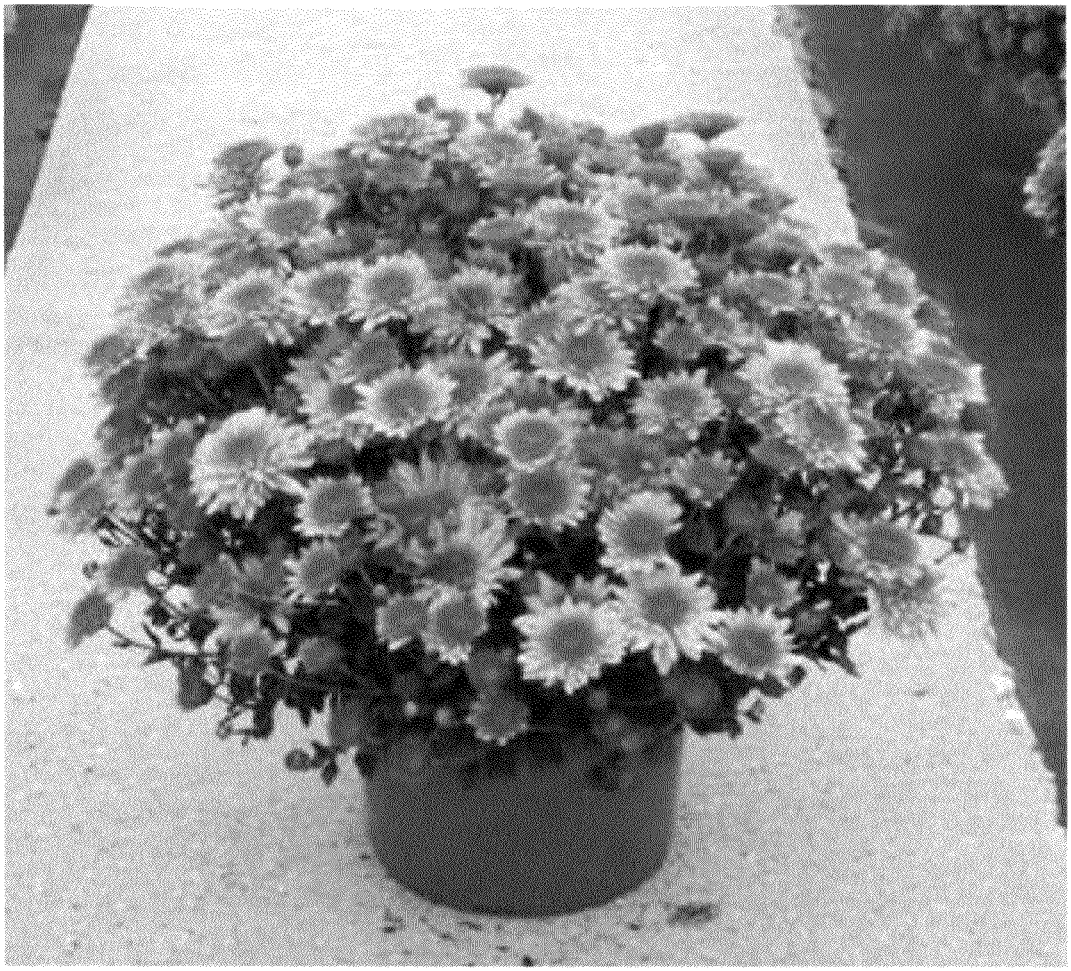

* * * * *